United States Patent [19]

Hartz, Jr.

[11] Patent Number: 5,478,747
[45] Date of Patent: Dec. 26, 1995

[54] IMMUNOLOGICAL SWITCH FOR CONTROLLING THE REPORTING OF TEST RESULTS

[75] Inventor: Thomas P. Hartz, Jr., Newark, Del.

[73] Assignee: E. I. Du Pont de Nemours and Company, Wilmington, Del.

[21] Appl. No.: 16,947

[22] Filed: Feb. 22, 1993

Related U.S. Application Data

[63] Continuation of Ser. No. 571,914, Aug. 17, 1990, abandoned, which is a continuation of Ser. No. 332,391, Apr. 3, 1989, abandoned, which is a continuation of Ser. No. 98,406, Sep. 18, 1987, abandoned.

[51] Int. Cl.$^6$ .................................................. G01N 35/00
[52] U.S. Cl. .............................. 436/45; 436/47; 436/809; 422/108
[58] Field of Search ........................... 422/57, 64, 68, 422/72, 108; 436/45, 47, 809

[56] References Cited

U.S. PATENT DOCUMENTS

| | | | |
|---|---|---|---|
| 4,043,756 | 8/1977 | Sommervold | 436/47 |
| 4,123,224 | 10/1978 | Givner et al. | 422/59 |
| 4,420,566 | 12/1983 | Jessop et al. | 436/46 |

*Primary Examiner*—Lyle A. Alexander

[57] ABSTRACT

Test reagents incorporate immunological materials capable of recognizing specific antigens or antibodies in test sample. The materials are selected to respond differently to a control product such that they are used as a switch to control the operation of an analytical instrument.

5 Claims, 2 Drawing Sheets

5,478,747

IMMUNOLOGICAL SWITCH FOR CONTROLLING THE REPORTING OF TEST RESULTS

This is a continuation of application Ser. No. 07/571,914 filed Aug. 17, 1990 now abandoned, which is a continuation of application Ser. No. 07/322,391, filed Apr. 3, 1989, which is a continuation of application Ser. No. 07/098,406, filed Sep. 18, 1987, now abandoned.

TECHNICAL FIELD

This invention relates to immunoassays and, in particular, to the use of immunoassays to control analytical testing.

BACKGROUND OF THE INVENTION

Analytical test systems, particularly those used in medical diagnostic applications, typically require routine quality control testing to assure that reported results are accurate. This is accomplished by running a sample of known analyte concentration in the test system and comparing the determined result with the known value for the sample. For test systems capable of performing assays for several analytes, each assay must be quality controlled routinely. Quality control samples with known values for multiple analytes are commercially available. In a multi-assay system, it often is possible to obtain all quality control results by running a single, multi-analyte, quality control sample.

In some multi-assay analyzers it may be desirable for commercial reasons to have the analyzer perform all available assays (y) on every sample but only allow reporting of results for a limited number (x) of the available assays. This is true typically in analyzers using a sealed reagent consumable such as an analyzer using a plastic centrifuge rotor having individual cells each containing a reagent for a different analytical test. Such an analyzer is sold by E. I. du Pont de Nemours and Company under the trademark Analyst. In this scenario, the analyzer operator could select which of the available assay results (up to x) he wishes to have reported. Consequently, even though all analytes are determined for a single sample, only a subset is reported. Unfortunately, there is no mechanism available to effect such result.

To obtain a quality control result for all assays on such a system, it would be necessary to provide plural rotors each having groups of reagents. The number of different rotors would be equal to the quotient of the number of assays available divided by the number of results reported with each run (y/x). Each group would contain control samples for the particular assays to be run for that group. This is undesirable because of increased cost and time required to prepare and run the number of determinations necessary to obtain a control result for each assay group. It would be desirable to provide a method of simultaneously providing a quality control assay for every analyte that may be tested in an analyzer and yet selectively provide test results when patient samples are run.

SUMMARY OF THE INVENTION

According to this invention, the result of an immunoassay generates a signal which is used to control the operation of an analytical device having plural test cells. One of the test cells of the device is provided with a reagent containing one component of a pair of materials necessary to effect an immunological assay (immunoassay). Thus, if a control sample containing the other component of the materials necessary for the immunoassay is subjected to the reagent, a signal is generated which, when detected by the device is used to control the device.

In a particular embodiment the response of this particular cell (a switch cell) provides an input to a software routine contained in a computer program written to control an instrument system capable of quantifying multiple analytes in a single sample. Thus by use of the switch cell, the values for all analytes may be reported when a quality control sample is run and only a limited, pre-selected subset of these analytes when a routine patient or test sample is run.

The method of this invention is used to control the operation of an analytical device capable of determining multiple analytes in a sample comprising the steps of performing an immunoassay to determine the presence and/or the concentration of a specific antibody or antigen in a test sample, comparing the result of the immunoassay to a defined threshold, reporting on all analyte determinations or only a subset of the determinations on the basis of the result of that comparison.

BRIEF DESCRIPTION OF THE DRAWINGS

The invention may be more fully understood from the following detailed description thereof taken in connection with accompanying drawings which form a part of this application and in which.

DESCRIPTION OF THE INVENTION

Figure 1:
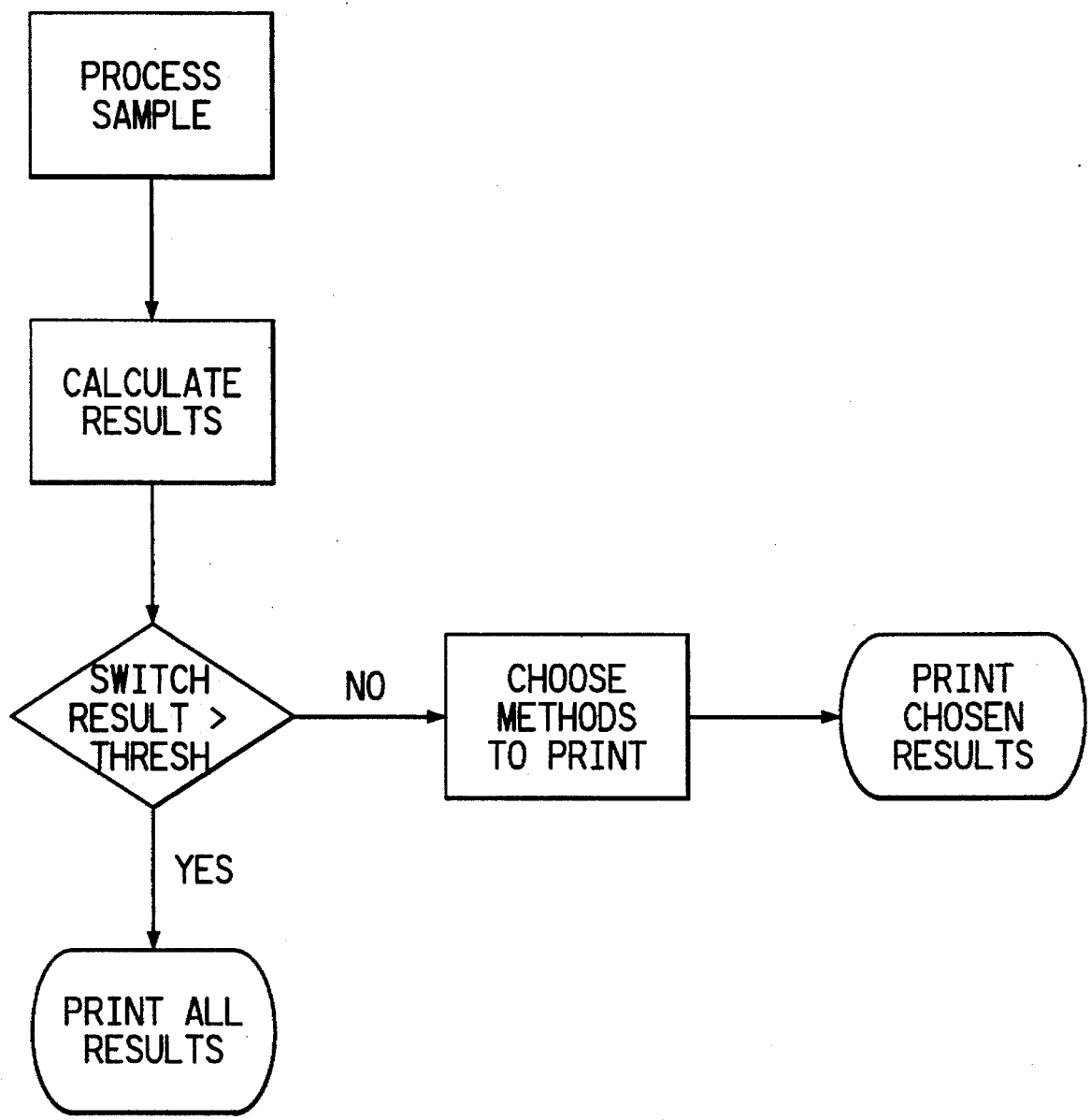
FIG. 1 is a generalized flow chart dipicting the method of this invention.

The specificity of the reaction between antibodies and antigens has been known for many years. ("Immunology," Bach, Ed.: Wiley, New York, 1982.) Antibodies are capable of binding to their homologous antigen even in the presence of closely related materials or in complex mixtures such as body fluids. Antibodies have been employed medically in both diagnostic and therapeutic applications.

In recent years, a number of immunoassay techniques have been developed for the measurement of ligands. Typically, a competitive binding immunoassay consists of a conjugate of a labeling substance linked to a binding component which participates in a binding reaction to produce two species of the labeled conjugate, a bound species and a free species. The relative amounts of the labeled conjugate that result in the bound species and the free species are a function of the concentration of the ligand to be detected in the test sample.

Where the labeled conjugate in the bound species and that in the free species are essentially indistinguishable by the means used to measure the labeling substance, the bound species and the free species must be physically separated. This type of assay is referred to as heterogeneous.

The two most widely used heterogeneous immunoassays are the radio immunoassay (RIA) and the enzyme linked immunosorbent assay (ELISA). In the RIA, a sample containing an unknown amount of antigen is mixed with a known amount of radiolabeled antigen and antibody. The system is allowed to react to near-equilibrium and then the antibody-bound antigen is separated from the unbound antigen. Since sample antigen competes with the labeled antigen for a limited number of antibody binding sites, the more antigen in the sample, the less labeled antigen is in the bound fraction (or the more is in the unbound fraction). This process is generally time-consuming (1–3 hours) and labor intensive.

RIA suffers from two major disadvantages: First, the labeling substance employed is a radioisotope which poses numerous problems associated with the handling, storage, and disposal. Second, RIA is performed in a competitive mode (i.e., the analyte and the labeled analyte compete for a limited number of binding sites on the antibody), and therefore the antibody affinity constant limits the sensitivity of the assay, typically in the range of $10^{-8}M^{-1}$ to $10^{-11}M^{-1}$.

ELIBA is similar in principle to RIA except that the labeling substance is an enzyme rather than a radioisotope. It still suffers from the limitation that sensitivity is a strict function of the antibody affinity constant.

Other labeling substances have been described in addition to isotopes and enzymes. These include fluorophores, coenzymes, bioluminescent materials, enzyme inhibitors, etc.

The second major class of immunoassays is referred to as homogeneous. Immunoassays in this class do not require separation of the bound species from the free species because the labeling substance in the bound species is distinguishable from the labeling substance in the free species. Examples of homogeneous immunoassays include the EMIT® assays (Syva Co.), fluorescence polarization immunoassays, agglutination or precipitation immunoassays such as PETINIA (particle enhanced turbidimetric inhibition immunoassay), etc.

The EMIT® assays rely on the use of an enzyme-analyte conjugate which has detectably different activity when antibody to analyte is bound to the conjugate versus free conjugate. The analyte in a sample competes with the enzyme-analyte conjugate for anti-analyte antibody. The higher the analyte concentration in the sample, the more free enzyme-analyte conjugate there is and therefore the higher the difference in enzyme signal.

Fluorescence polarization immunoassays are based on the change in the fluorescence polarization properties of an analyte-fluorescer conjugate when it is bound to an anti-analyte antibody versus when the conjugate is free. The analyte in the sample competes with the analyte-fluorescer conjugate for the anti-analyte conjugate. The higher the analyte concentration in the sample, the more free analyte-fluorescer conjugate.

Precipitation assays rely on the ability of the divalent antibodies to cross-link larger ligands, such as bovine serum albumin, and therefore cause precipitation. This precipitation can be detected as a change in turbidity of the sample.

This invention makes use of the ability of immunoassays to detect particular analytes to act as an immunological switch in analytical instruments. In many analytical instruments, plural analytes are determined from a given sample. One such instrument is the Analyst™ Benchtop Chemistry System sold by E. I. du Pont de Nemours and Company, Wilmington, Del.

The Du Pont Analyst™ Benchtop Chemistry System is an instrument designed to provide clinical assay results for patient samples. The instrument processes reagent rotors which contain 24 reagent wells distributed around the circumference of the rotor. Each well may contain a reagent tablet which includes the assay reagents required to perform an analytical test. The center of the rotor serves as a sample introduction/incubation chamber. The chamber is divided into two compartments which permits the introduction of two different samples or two dilutions of the same sample. Each reagent well is isolated from the others to permit multiple analytes to be determined simultaneously with a single rotor. The sample is introduced to the reagent wells by centrifugation of the rotor. Assays are monitored spectrophotometrically according to processing parameters programmed into the instrument. Results are reported by the instrument according to further programming instructions.

The instrument is designed to report the results of a subset of the multiple analytical tests distributed in the wells of certain rotors. The operator chooses which results are to be reported up to a maximum of three results. For ease of explanation the invention will be described in conjunction with an Analyst™ instrument.

A multi-analyte quality control product containing all of the analytes to determined by the instrument is provided. The operator is instructed to assay the control product on a regular basis as part of the quality control program for the instrument. By maintaining a record of the results obtained for the control product, it is possible to detect changes in system performance which may adversely affect patient sample results. The maintenance of such a quality control record is typically a requirement of clinical laboratory regulating agencies.

In accordance with this invention, the quality control product includes a material containing one of the components of an immunoassay in the diluent matrix to stabilize the solution, enhance solubility, and to mimic a sample with regard to matrix effects. The other component of an immunoassay is placed in one of sample cells which is to act as an immunological switch. By selecting the control product immuno component to be different from the immuno component in the samples, such that only the control product can effect the switch, the instrument operation may be controlled to act differently for the control product than it would for a sample. Thus the immunological switch can permit the reporting of all chemistry results from the rotor if a quality control product is run as sample but allows the reporting of only up to three results if a patient sample is assayed.

As noted, this invention is intended to detect and/or quantitate a component contained in a quality control product and then to use the result of the immunoassay as a software switch. Computer software routines are able to respond at a decisional branchpoint to the prompt "if ... then ..." to initiate different branch. Frequently these prompts are inserted to enable the program to follow one of two separate paths depending on the results of an observation, bits of data or previous calculation. Such components should not be present in typical test samples or should be present in test samples only in quantities which permit test samples to be distinguished from quality control samples. The test systems which use this invention are capable of determining multiple analytes on a single sample and reporting only a subset of results determined. This subset is pre-selected by the operator. The control products used in this invention contain multiple analytes capable of being assayed by the test system.

A flow chart describing a general software routine which implements this invention is presented in FIG. 1. In FIG. 1, the immunological switch is one which causes all results to be printed if a threshold value is exceeded.

FIG. 1 shows a general flow chart for processing and software routine to demonstrate this invention. The control sample is processed the same as any other sample using the usual instrument parameters. The instrument would calculate the assay results in the normal manner and would then compare the result for the switch assay to a threshold value. If this logical comparison evaluates to true, then the instrument prints results for every assay run on that sample. If the logical comparison evaluates to false, then the instrument prompts the operator to choose a certain number of assays to have the results printed and then the instrument prints the results of those assays.

An advantage of this invention is that quality control of all assays for which analytes are contained in the quality control product can be accomplished with a single run. This saves the operator the time and expense associated with multiple runs.

In operation, sample is added to an Analyst™ Select rotor or similar analytical device with multiple cells for determining several analytes in a single sample and the rotor is placed in the Analyst™ instrument for processing. The Analyst™ instrument reads the barcode on the rotor to determine the type of rotor being processed. Only Select rotors are provided with the immunological switch of this invention. The Analyst™ instrument brings the rotor up to temperature while gently mixing the sample with the diluent. After temperature equilibration, the rotor is brought up to high speed, stopped quickly, brought up to speed, stopped quickly. This is repeated several times to dissolve the tablets contained in each cell and to mix the contents of the cell with the sample. The Analyst™ instrument then measures the absorbance values of each cell and performs a cell-by-cell calculation of the polished absorbance values using predetermined calculation subroutines contained in the software. The Analyst™ instrument then calculates an analyte result value for each assay contained in the rotor. At this point, the software routine uses the identification of the rotor obtained during the bar code read step. If the identification for a Select rotor is false, then the Analyst™ instrument prints all results of all assays on that rotor. If the Select rotor identification is true, then the switch cell assay value is compared to a threshold value contained in memory. If the switch cell value is greater than the threshold value, the logical expression evaluated to true; and, again, all assay results are printed. If the switch cell value comparison evaluates to false, the software checks to see if a default flag is on. If the default flag is on, then the Analyst™ instrument prints the results for three pre-selected, default tests. If the default flag is off, then the Analyst™ instrument prompts the operator to select three of the assays on that rotor and then prints the results for those three assays.

Figure 2:
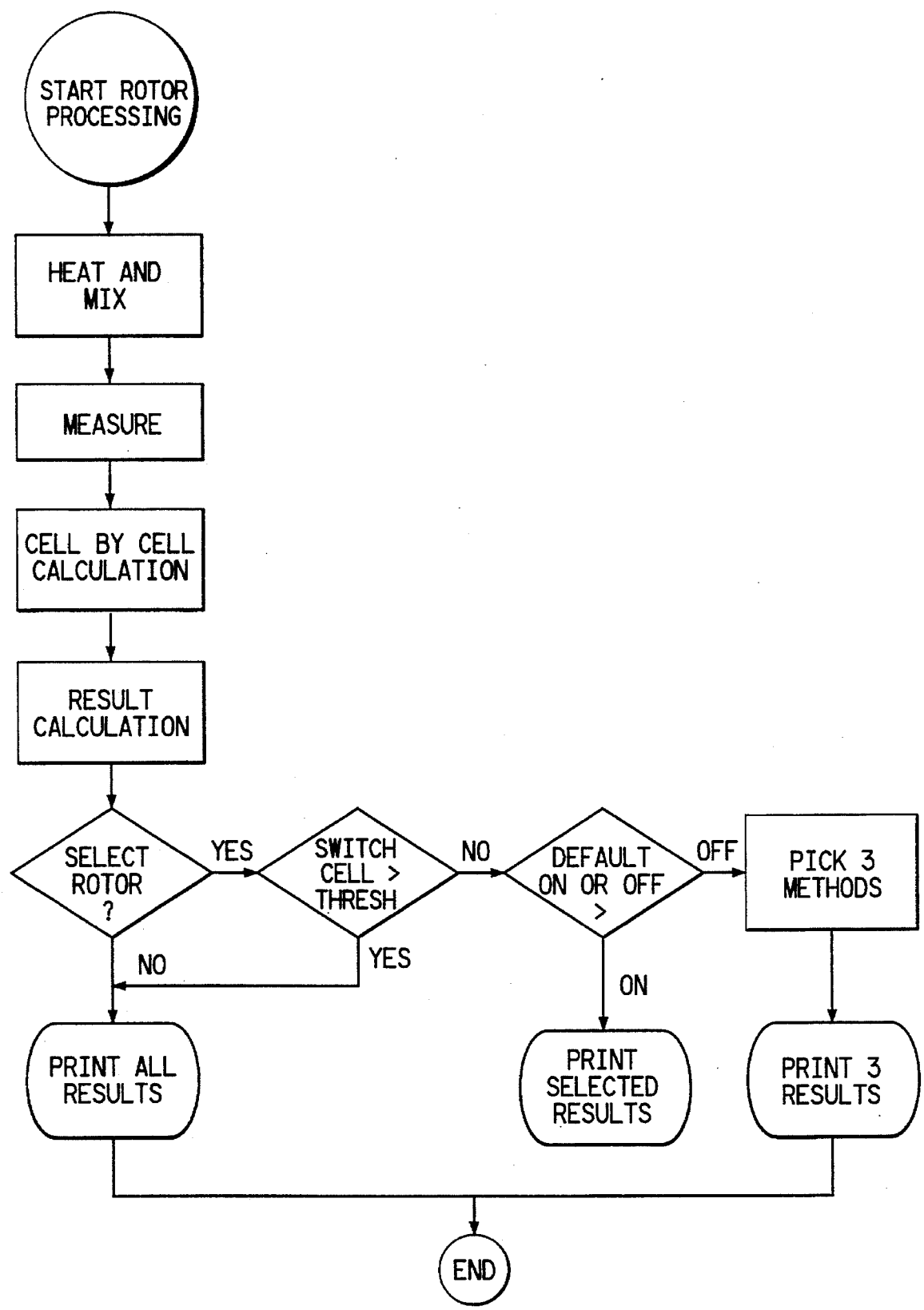
FIG. 2 is a detailed flow chart of a computer program designed to implement the method of this invention.

The software routine for reporting results for the assays included in the Analyst™ rotor includes a subroutine which reports all assay results if a rate of turbidity formation is observed in the cell containing the dissolved tablet which exceeds 10 milli-absorbance units/minute. If the observed rate is less than 10 mA/min, up to three results can be requested or, if the default switch is activated, a pre-selected group of up to three results is reported (refer to FIG. 2).

By way of example, a reagent tablet containing polyethylene glycol, a detergent, a buffer, salt, an excipient, and a quantity of an antibody which recognizes bovine serum or a component of bovine serum antigenically distinct from human serum can be used for the immunological switch. Bovine serum is used with the control sample. These tablets are dissolved during the processing of the Analyst™ Select rotor with 35 uL of diluted sample i.e. human or bovine serum. Since only the control product contains the Bovine serum, only it can trigger the immunological switch by causing a precipitater which when detected triggers the switch. Table 1 includes the final concentration achieved for each of these components when the tablet is dissolved in the rotor. Those familiar with the arts of Physical Pharmacy, Immunology, or Biochemistry may identify other components or identify other quantities of these components which would function equivalently. The quantity of antiserum added to the tablet is dependent on the potency of the particular lot of antiserum: the quantity of excipient added is adjusted on the basis of the solids content of the antiserum to yield a tablet of the weight desired.

EXAMPLE I

Table 1 lists the specific materials and quantities of components used for anti-bovine serum albumin tablets. These anti-bovine serum albumin tablets find use in precipitation assays which rely on the ability of the divalent antibodies to cross-link larger ligands, i.e., bovine-serum albumin. As in Table 1, a 7.0 mg tablet is prepared. A spray-freeze process described in U.S. Pat. No. 3,721,725, issued Mar. 20, 1973, to Briggs, et al., was used to prepare the tablets.

TABLE 1

ANTI-BOVINE SERUM ALBUMIN TABLET FORMULATION

| COMPONENT | MATERIAL USED | QTY/TABLET (MG) | RECONSTITUTED CONCENTRATION |
| --- | --- | --- | --- |
| Polyethylene glycol | PEG 4000 | 0.78750 | 2.25% |
| Detergent | Tween-20 ™ | 0.04725 | 0.135% |
| Salt | NaCl | 0.46029 | 0.225M |
| Buffer | Tris, pH 7.4 | 0.23791 | 0.045M |
| Excipient | Trehalose | 4.75445 | — |
| Anti-bovine serum | Goat anti-bovine serum, IgG fraction | 0.71260 | — |
| | | 7.00000 | |

Processing of this tablet by the Analyst™ instrument yields a reaction mixture which demonstrates a rate of turbidity formation in the presence of Analyst™ control products and may be followed spectrophotometrically at 340 nm. No significant rate of turbidity formation is observed with human serum samples. Table 2 summarizes the results obtained with anti-bovine serum tablets in Select rotors for human serum samples and quality control products.

TABLE 2

RESULTS OBSERVED WITH ANTI-BOVINE SERUM TABLETS

| SAMPLE | n | MEAN RATE (mA/min) | STD. DEV. (mA/min) |
| --- | --- | --- | --- |
| Human serum individual samples | 22 | −4.82 | 8.19 |
| Control Product 1 Du Pont lot 222-046 | 39 | 31.3 | 5.90 |

TABLE 2-continued

RESULTS OBSERVED WITH ANTI-BOVINE SERUM TABLETS

| SAMPLE | n | MEAN RATE (mA/min) | STD. DEV. (mA/min) |
|---|---|---|---|
| Control Product 2 Du Pont lot 223-046 | 39 | 21.2 | 4.33 |

EXAMPLE II

As an alternative to the bovine serum albumin/anti-bovine serum albumin reaction used in Example 1, one could use the keyhole limpet hemocyanin/anti-keyhole limpet hemocyanin reaction as described below.

Hemocyanin derived from keyhole limpets (KLH, available from Calbiochem and several other sources) would be added to a multi-analyte control product such as the Analyst™ control to a final, reconstituted concentration of about 0.2 mg/mL. The quantity of anti-KLH antibody (available from Cooper Biomedical. Cappel Division) required to give an appropriate turbidity response when mixed with the control would be determined by a titration experiment in which dilutions of an antibody concentrate in buffer are added to samples of the control which contains the KLH. This titration experiment could performed in an all liquid system by adding dilutions of the antibody concentrate to solutions containing the control. 3.0% (w/v) polyethylene glycol 4000, 0.15% Tween-20 (polyoxyethylenesorbitan monolaurate from Sigma Chemical Company), 0.05M Tris(hydroxymethly)aminomethane buffer(ph=7.0), 0.25M sodium chloride and trehalose (Sigma Chemical Company) as excipient. The amount of trehalose is dependent on the solids content of the anti-KLH antibody. Turbidity formation would be followed spectrophotometrically and the antibody dilution which gives an appropriate turbidity response would be used to calculate the amount of antibody to put in the reagent tablet.

A reagent tablet containing the appropriate amount of antibody would be made as described in Example 1. This tablet could then be placed in an Analyst™ Select rotor and processed as in Example 1. The use of the KLH spiked control material as a sample would then cause a turbidity higher than the threshold value in the switch cell and the Analyst™ would report all assay results. Patient samples do not contain KLH and would not give rise to detectable turbidity in the switch cell so the Analyst™ would report the values for the default assays if the default flag was set or would otherwise prompt the operator for the assays to report.

What is claimed:

1. A method for controlling the number of different analytical determinations reported by an analytical device, having a plurality of test cells and capable of making multiple different analytical determinations using immunoassays on a sample, using the, result of a single immunoassay within said analytical device, said immunoassay having at least first and second reagents, the method comprising the steps of:

positioning a first reagent of the immunoassay in a test cell within the analytical device;

performing an immunological analysis on a test sample having the second reagent of the immunoassay;

comparing the result of the immunoassay for the test sample with a defined threshold quantity;

reporting all multiple different analytical determinations on the test sample if the detected immunoassay exceeds the threshold quantity; and reporting only a subset of the multiple different analytical determinations if the detected immunoassay fails to exceed the threshold quantity.

2. The method set forth in claim 1 wherein the analytical device includes a rotor having a central portion having a sample to be tested and a peripheral portion having the plural test cells each communicating with the central portion reagent, the test sample being introduced into the respective cells from the central portion upon rotation of the rotor, comprising the additional steps of using an antibody for the first reagent immunoreagent and a homologous antigen for the second reagent.

3. The method set forth in claim 2 wherein the test sample includes Keyhole limpet hemocyanin and the immunoreagent includes an anti-Keyhole limpet hemocyanin antibody.

4. The method set forth in claim 2 wherein the test sample contains bovine serum proteins and the immunoreagent contains an antibody for bovine serum protein.

5. The method set from in claim 2 wherein the test sample contains an antibody or antigen normally not found in samples to be tested.

* * * * *